(12) United States Patent
Sah et al.

(10) Patent No.: US 10,598,617 B2
(45) Date of Patent: Mar. 24, 2020

(54) METROLOGY GUIDED INSPECTION SAMPLE SHAPING OF OPTICAL INSPECTION RESULTS

(71) Applicant: KLA-Tencor Corporation, Milpitas, CA (US)

(72) Inventors: Kaushik Sah, Kessel-Lo (BE); Andrew James Cross, Cheshire (GB); Antonio Mani, Leuven (BE)

(73) Assignee: KLA-Tencor Corporation, Milpitas, CA (US)

(*) Notice: Subject to any disclaimer, the term of this patent is extended or adjusted under 35 U.S.C. 154(b) by 119 days.

(21) Appl. No.: 15/671,230

(22) Filed: Aug. 8, 2017

(65) Prior Publication Data

US 2018/0321168 A1 Nov. 8, 2018

Related U.S. Application Data

(60) Provisional application No. 62/502,459, filed on May 5, 2017.

(51) Int. Cl.
| | |
|---|---|
| *G06K 9/00* | (2006.01) |
| *G01N 23/2251* | (2018.01) |
| *H01L 21/66* | (2006.01) |
| *G01N 21/956* | (2006.01) |
| *G01N 21/88* | (2006.01) |
| *G01N 21/95* | (2006.01) |

(52) U.S. Cl.
CPC ......... *G01N 23/2251* (2013.01); *H01L 22/20* (2013.01); *G01N 21/9501* (2013.01); *G01N 21/95607* (2013.01); *G01N 2021/8867* (2013.01); *H01L 22/12* (2013.01)

(58) Field of Classification Search
None
See application file for complete search history.

(56) References Cited

U.S. PATENT DOCUMENTS

| | | | |
|---|---|---|---|
| 6,121,156 | A | 9/2000 | Shamble et al. |
| 6,171,737 | B1 | 1/2001 | Phan et al. |
| 6,408,219 | B2 | 6/2002 | Lamey, Jr. et al. |
| 6,701,259 | B2 | 3/2004 | Dor et al. |
| 6,744,266 | B2 | 6/2004 | Dor et al. |
| 6,803,554 | B2 | 10/2004 | Ye et al. |
| 7,207,017 | B1 | 4/2007 | Tabery et al. |

(Continued)

OTHER PUBLICATIONS

Lagus, et al., Advanced SEM-based metrology of systematic defects, IEEE Symposium on Semiconductor Manufacturing, 2005, pp. 465-468 Sep. 13, 2005.

(Continued)

*Primary Examiner* — Hadi Akhavannik
(74) *Attorney, Agent, or Firm* — Hodgson Russ LLP

(57) ABSTRACT

Information from metrology tools can be used during inspection or review with a scanning electron microscope. Metrology measurements of a wafer are interpolated and/or extrapolated over a field, which creates modified metrology data. The modified metrology data is associated with defect attributes from inspection measurements of a wafer. A wafer review sampling plan is generated based on the defect attributes and the modified metrology data. The wafer review sampling plan can be used during review of a wafer using the scanning electron microscope.

16 Claims, 5 Drawing Sheets

(56) References Cited

U.S. PATENT DOCUMENTS

| | | | |
|---|---|---|---|
| 7,853,920 B2 | 12/2010 | Preil et al. | |
| 7,962,866 B2* | 6/2011 | White | G06F 17/5081 700/110 |
| 8,429,570 B2* | 4/2013 | Bailey | G06F 17/5081 716/51 |
| 8,495,527 B2* | 7/2013 | Bailey | G06F 17/5081 716/53 |
| 9,201,022 B2 | 12/2015 | Hu et al. | |
| 2003/0223630 A1* | 12/2003 | Adel | G03F 7/705 382/145 |
| 2008/0167829 A1 | 7/2008 | Park et al. | |
| 2011/0170091 A1* | 7/2011 | Chang | G01N 21/9501 356/237.5 |
| 2011/0202298 A1* | 8/2011 | Izikson | H01L 22/20 702/83 |
| 2013/0035888 A1* | 2/2013 | Kandel | G03F 7/70633 702/81 |
| 2014/0031968 A1* | 1/2014 | Baseman | G05B 13/048 700/121 |
| 2014/0301630 A1 | 10/2014 | Kulkarni et al. | |
| 2015/0029499 A1* | 1/2015 | Wright | G01N 21/9501 356/237.5 |
| 2017/0059491 A1 | 3/2017 | Duffy et al. | |

OTHER PUBLICATIONS

Khvatkov, et al., Automated metrology for SEM calibration and CD line measurements using image analysis and SEM modeling methods, Proc. SPIE 6922, Metrology Inspection, and Process Control for Microlithography XXII, p. 69222N, 12 pages Mar. 24, 2008.

Levi, et al., SEM Simulation for 2D and 3D Inspection Metrology and Defect Review, Proc. of SPIE 9051, Advances in Petterning Materials and Processes XXXI, p. 90510B, 10 pages Apr. 2, 2014.

ISA/KR, International Search Report and Written Opinion for PCT/US2018/031002 dated Sep. 21, 2018.

\* cited by examiner

METROLOGY GUIDED INSPECTION SAMPLE SHAPING OF OPTICAL INSPECTION RESULTS

CROSS-REFERENCE TO RELATED APPLICATIONS

This application claims priority to the provisional patent application assigned U.S. App. No. 62/502,459 filed May 5, 2017, the disclosure of which is hereby incorporated by reference.

FIELD OF THE DISCLOSURE

This disclosure relates to wafer inspection.

BACKGROUND OF THE DISCLOSURE

Evolution of the semiconductor manufacturing industry is placing ever greater demands on yield management and, in particular, on metrology and inspection systems. Critical dimensions are shrinking while wafer size is increasing. Economics is driving the industry to decrease the time for achieving high-yield, high-value production. Thus, minimizing the total time from detecting a yield problem to fixing it determines the return-on-investment for the semiconductor manufacturer.

Wafers can be inspected using a variety of techniques typically based on optical methods or scanning electron microscopes (SEM). Previously, broad band plasma (BBP) attributes were used to determine SEM inspection sampling. Metrology inputs were not used.

As design nodes continue to shrink, the optical signal-to-noise ratio for subtle failures of hotspots is becoming a more challenging issue. A hot inspection (e.g., an inspection in which a threshold for determining presence of a potential defect is substantially close to a noise floor of the inspection) can be run and then various attributes of captured defects can be used to perform an elaborate sample for SEM verification. However, this can be an extremely expensive technique. Although a hot inspection can increase the likelihood of detecting defects of interest, it is at the expense of substantially high nuisance rates. Less than 5,000 defects may be sampled from over one million defects detected by optical inspection. These process variations typically occur as a function of wafer level or exposure field level fluctuations. There also are limited possibilities of guided SEM review or SEM inspection without optical inspection because there is limited information about which wafer/field areas to look into.

Therefore, improved techniques and systems for SEM inspection and review are needed.

BRIEF SUMMARY OF THE DISCLOSURE

In a first embodiment, a method is provided. Metrology measurements and inspection measurements are received at a controller. The metrology measurements and inspection measurements are of one or more wafers. Using the controller, the metrology measurements are interpolated and/or extrapolated over a field of a wafer thereby creating modified metrology data. Defect attributes from the inspection measurements are associated with the modified metrology data using the controller. A wafer review sampling plan is generated based on the defect attributes and the modified metrology data using the controller.

An inspection with a scanning electron microscope of the wafer or a different wafer may be performed based on the wafer review sampling plan.

The modified metrology data may be a uniform grid across the wafer.

The interpolating can include local linear interpolation or a model based approach.

The metrology measurements can be for an entire surface of the wafer and the interpolating can be across the entire surface of the wafer.

The metrology measurements can include at least one of overlay, dose, focus, critical dimension, and topography.

The field may be an entire surface of the wafer.

In a second embodiment, a system is provided. The system comprises a controller in electronic communication with a scanning electron microscope and a metrology tool. The controller includes a processor and an electronic data storage unit in electronic communication with the processor. The controller is configured and/or programmed to: receive metrology measurements and inspection measurements; interpolate and/or extrapolate the metrology measurements over a field of a wafer thereby creating modified metrology data; associate defect attributes from the inspection measurements with the modified metrology data; and generate a wafer review sampling plan based on the defect attributes and the modified metrology data. The metrology measurements and inspection measurements are of one or more wafers.

The controller can be configured and/or programmed to transmit the wafer review sampling plan to the scanning electron microscope.

The metrology measurements can include at least one of overlay, dose, focus, critical dimension, and topography.

In a third embodiment, non-transitory computer readable medium is provided. The non-transitory computer readable medium stores a program configured to instruct a processor to: interpolate and/or extrapolate metrology measurements over a field of a wafer thereby creating modified metrology data; associate defect attributes from inspection measurements of the wafer with the modified metrology data; and generate a wafer review sampling plan based on the defect attributes and the modified metrology data. The metrology measurements and inspection measurements are of one or more wafers.

The modified metrology data may be a uniform grid across the wafer.

The interpolating can include local linear interpolation or a model based approach.

The metrology measurements can be for an entire surface of the wafer and the interpolating can be across the entire surface of the wafer.

The metrology measurements can include at least one of overlay, dose, focus, critical dimension, and topography.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Metrology tools carry information on process variation that can lead to subtle failures. This information from the metrology tools can be used to improve SEM review and reduce false rate. This approach can also shed light into root causes for defect formation (e.g., is the hotspot linked to overlay drift, CD drift, or both) and narrow down the exhaustive root cause analysis methods. Also, use of metrology inputs or other inputs can provide a guided SEM review or inspection, even in the absence of optical inspection results.

Embodiments of the techniques and systems disclosed herein can enable more comprehensive and representative SEM sampling from optical defect inspection results by taking inputs from overlay and optical critical dimension (OCD) tools for access to overlay, CD, dose, and focus metrology data, respectively. This can target design hotspots or perform other functions. High spatial density sampling measurements obtained from metrology tools can provide additional attributes for design hotspot sampling not only across wafer, but also at an intra-field level. This can flag areas of higher variations than desired or expected by the nominal process. By using existing optical attributes, SEM sampling can be improved for hotspot discovery by including these across-wafer or intra-field effects in both the discovery of new types of patterns of interest as well as their effect on the process window. This sampling approach also can be used to monitor known hotspots more effectively.

Figure 1:
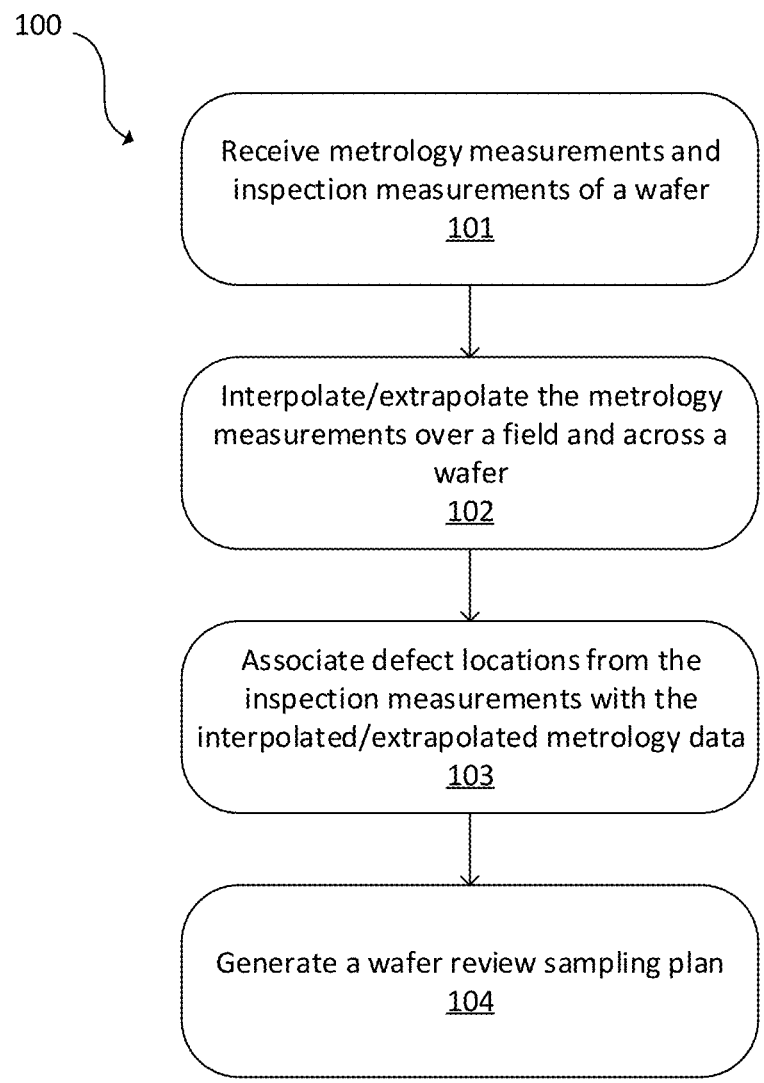
FIG. 1 is a flowchart of an embodiment of a method in accordance with the present disclosure.

FIG. 1 is a flowchart of a method 100. At 101, metrology measurements and inspection measurements of one or more wafers are received at a controller. The metrology and inspection measurements can be of the same wafer or of different wafers. The measured data can be in the form of a list with measured coordinates and values. The metrology measurements can include at least one of overlay, dose, focus, CD, and topography (e.g., nano-topography, wafer surface flatness, etc.). This technique also can use measurements from other metrology tools with different types of metrologies related to defect formation than those listed.

As an example of measured data, an image is obtained by processing the instrument output of a tool. The tool output is typically in the form of a list where a measurement (e.g., metrology of a physical dimension such as CD, overlay, local in plane displacement, etc.) or inspection attribute (e.g., detection of a defect) is reported together with its location (e.g., coordinate) on the wafer.

Thus, metrology data can come as one or more values (e.g., X, Y). A grid is a function of the sampling utilized for data collection. Uniform or sparse sampling plans may be used. Interpolation may be needed for those cases where a metrology attribute needs to be estimated in between two different existing sampled locations, given an initial regular grid. Extrapolation may be needed when the initial sampling grid is non-regular, sparse, and/or asymmetric.

In an instance, dense overlay and OCD measurements are obtained for a wafer. Examples of these measurements can be seen in the exemplary CD data of FIG. 2 and the exemplary overlay data of FIG. 3.

Figure 2:
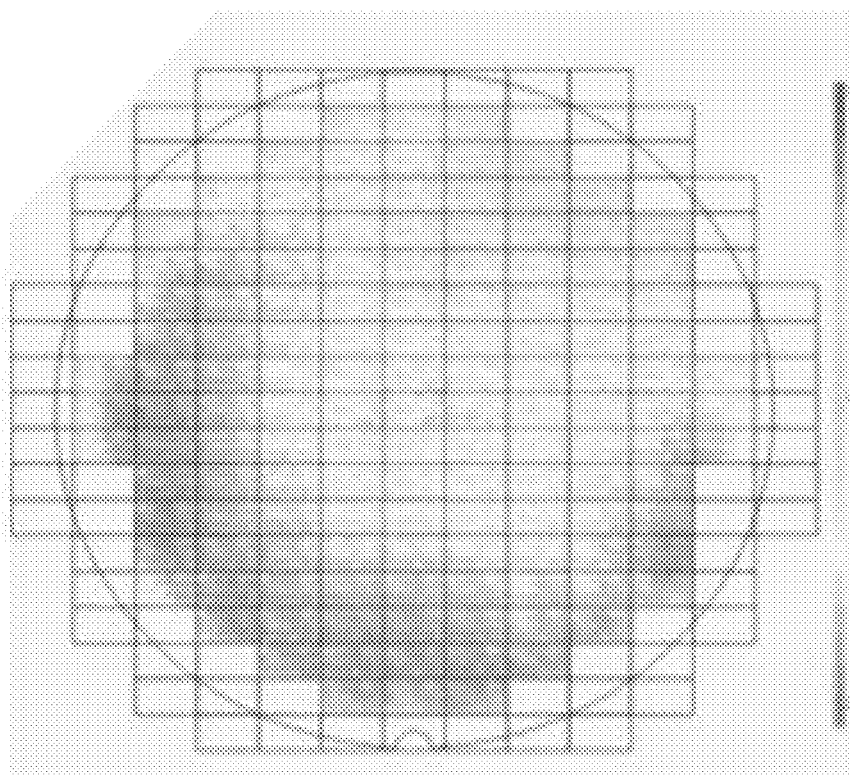
FIG. 2 is exemplary critical dimension (CD) data showing a wafer level fingerprint.
Figure 3:
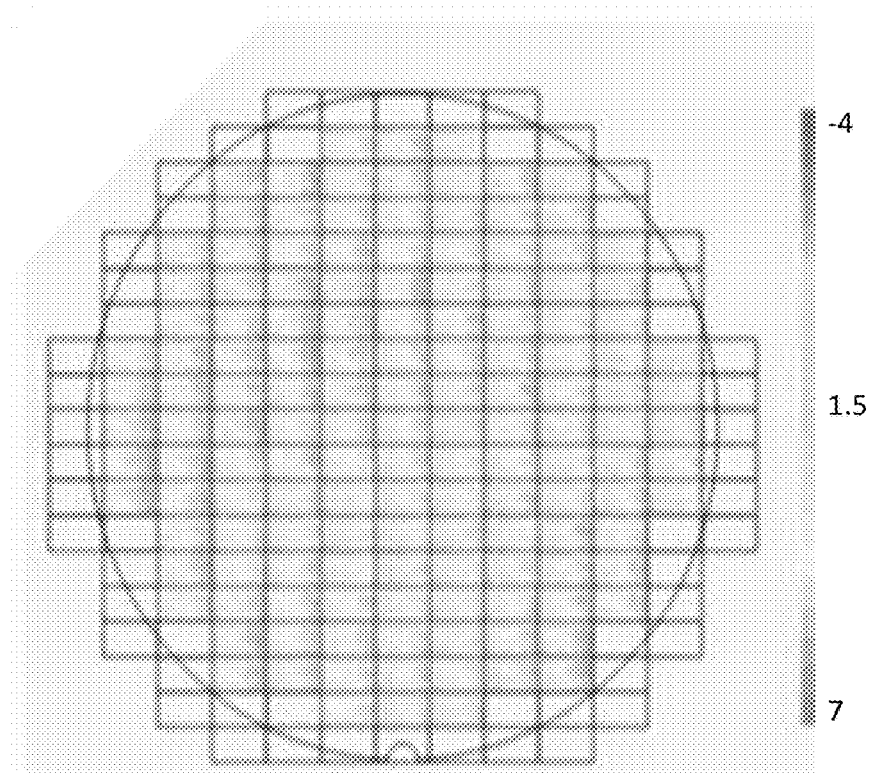
FIG. 3 is exemplary overlay data showing intra field and wafer level signature.

Turning back to FIG. 1, the metrology measurements are interpolated and/or extrapolated using the controller at 102. The metrology measurements may be interpolated and/or extrapolated over a field of a wafer thereby creating modified metrology data. The metrology measurements may be interpolated and/or extrapolated over the same wafer that generated the metrology measurements or a different wafer. The interpolation or extrapolation can occur using a suitable resolution. In an instance, interpolation is across an entire wafer. There may be across-wafer and intra-field variations, as seen in FIGS. 2-3 for CD and overlay, respectively.

Extrapolation also can be performed for points lying beyond measurement extents. Extrapolation can be used if metrology values are to be extended beyond measured locations (extent). The specific distribution of metrology values may depend on wafer scale phenomena and field-scale phenomena due to the nature of a lithography process, which repeats the printing of a field across a full wafer; etch, which etches a full wafer at once; and their mutual interaction in contributing to the final observed metrology attribute distribution. For example, if given an initial screening sampling (e.g., sparse or asymmetric) where the field level distribution of sampled points is unbalanced to the left, an extrapolation at field level to obtain data for the right side of the field (non-sampled) will be needed. Interpolating between the mentioned points and any other point pertaining to an adjacent field can be used to estimate wafer level distribution of the metrology data, but may not be as useful for estimating field level distribution. Thus, field level extrapolation may be needed.

Metrology data may be divided into a grid with defined resolution. This can be done during the interpolation/extrapolation step. A model based approach can be used, where once a model is inferred based on actual measurements, the interpolation can be continuous and directly transferred to optical inspection coordinates without needing an explicit grid.

The estimation of the metrology measurements may include local linear interpolation, a model based approach, probability distribution, or other techniques. In local linear interpolation, triangulation is followed by linear interpolation. In a model based approach, translational, rotational, or skew based terms may be present. A model based approach can include linear regression of a physical model and can revert to the compact model form at desired locations. Statistical methods can be used to determine the probability distribution as a function of spatial coordinates and solving for the density function associated with it. Model parameters can be determined by optimizing a loss function (e.g., least square error) on the measured data. A goal can be to estimate metrology values at locations where actual measurement was not possible that are in device yield critical areas of the device on the wafer.

The modified metrology data may be a uniform grid across the wafer. For example, the grid may be 1 mm by 1 mm, but other values are possible. Smaller grids may be used, but these can affect interpolation in certain instances. In case of model based approach, grid size need not be explicitly defined and calculation of metrology values can be done directly on optical inspection (or any other predetermined set) coordinates using the model by solving the model expression with coordinates of interest as inputs.

In an example, the metrology measurements may be for an entire surface of the wafer and the interpolating may be across the entire surface of the wafer.

Interpolation/extrapolation also can include defining explicit metrics using various metrology measurements, if applicable, such as combining overlay and CD measurements.

The metrology data attributes associated with specific defects can be used as for review sampling. At 103, defect attributes from the inspection measurements are associated with the modified metrology data using the controller. The inspection measurements may be aligned to the modified metrology data. This can be achieved by correcting the offset between wafer center and field corners between inspection and metrology measurements.

The defect attributes can be a location or other data. The defect locations can provide coordinates for interpolation and/or extrapolation and, consequently, metrology association. However, the defect attributes can be any property of a defect reported by an inspection tool or other semiconductor processing tool including defect signal, noise, energy, polarity, shape, roughness, brightness, background design info, or other information.

Figure 6:
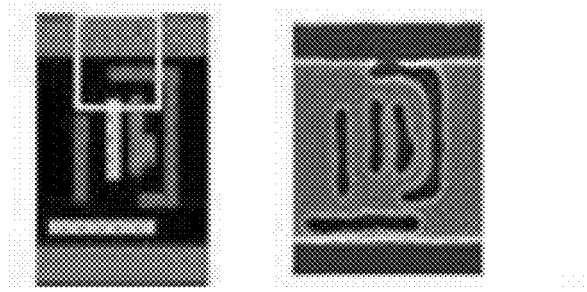
FIG. 6 shows a design clip (left) and SEM image of an exemplary hotspot (right)

A local linear approach or other techniques (in case of grid based interpolation) and direct calculation (in case of model based approach) may be used to associate defects with modified metrology data. FIG. 6 shows a design clip (left) and SEM image (right) of an exemplary hotspot where all design instances over the whole layout were inspected optically. The optical inspection result in FIG. 4 belong to this hotspot. However, any number of hotspots can be included. No prior hotspot information may be needed. Inspection can be done on the whole field (layout).

Figure 7:
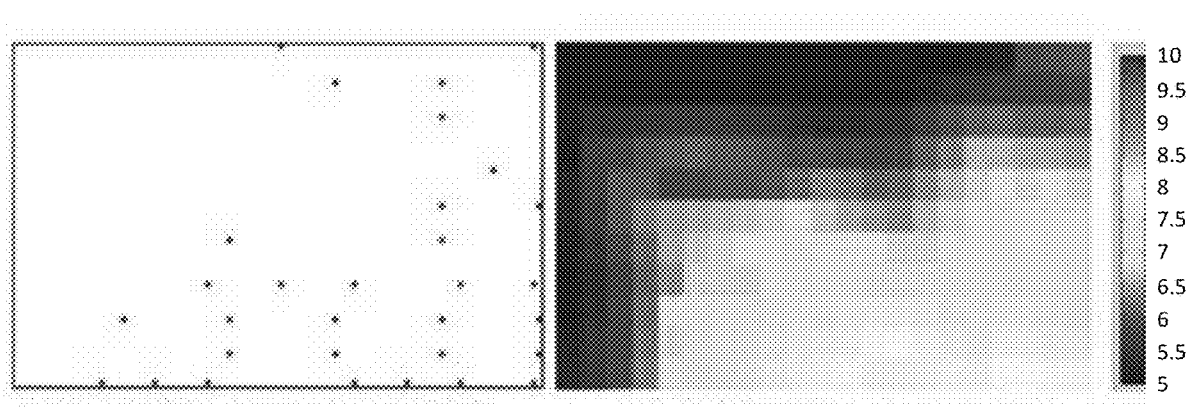
FIG. 7 shows post SEM review killer signature for an example field (left) and dense overlay measurement on the same field showing high degree of correlation (right)

FIG. 7 shows post SEM review killer signature for an example field (left) and dense overlay measurement on the same field showing high correlation (right). Each defect on the left is associated with a reading on the right. Thus, each defect attribute is associated with metrology data. Locations where the magnitude of the overlay vector (in this case one of its components) is high can exhibit defect formation trends coherent with the overlay magnitude. In an example, to associate defect attributes with metrology data, locations where overlay errors are high result in defect formation as verified by SEM.

At 104, a wafer review sampling plan is generated using the controller. The wafer review sampling plan can be based on the defect attributes and the modified metrology data. A wafer review sampling plan can be generated using algorithms based on multiple defect attributes. Defect attribute space may not be extended to include metrology values. Rather, it can be flexible. Constraints like a maximum number of defects to a sample can be defined in advance. Thus, wafer review sampling plans can be customized.

A wafer review sampling plan may be a list of locations to go and capture images for further discovery, root causing, and classification of failure. The input for the controller to generate the wafer review sampling plan may be an area of the wafer, out of which can be extracted prioritized locations based on algorithms that extract high risk locations based on the metrology input, the defect optical attributes, and/or the geometrical properties of the design.

The review sampling plan can be weighted to particular areas on a wafer, such as those with the highest variation. The metrology attributes can shape the review sampling plan, which can make the review less random and reduce false instances. Relationships within a die or across a wafer can be accounted for.

In an instance, sampling can be biased to defects having extreme CD and/or overlay error values. A defined attribute combining the CD, overlay, wafer shape, and surface nano-topography attributes into a single formula (metric) can also be used during sampling.

In another instance, the wafer edge has high CD variation. The wafer review sampling plan may be biased toward the wafer edge.

In another instance, there is a high intra-field effect across the wafer. The wafer review sampling plan may be focused on particular areas of the field.

In yet another instance, there is a high variance in metrology data die to die. The wafer review sampling plan may be focused on particular areas of the die.

In addition, there may be combinations of such effects leading to weighted sample for specific areas with a field and across the wafer.

In yet another instance, field or wafer level distribution of metrology data may be used to obtain confidence levels and define outliers.

In yet another instance, sampled locations can be used to guide optical inspection tools further for a targeted inspection. The sampled locations can be further analyzed based on their background design and, if collected, SEM images to highlight critical regions of the device. These regions can then be optically inspected for efficient defect monitoring across wafers or to discover new hotspots. In the absence of prior optical inspection, a grid based estimation of metrology measurements can be used to determine sample locations.

At 104, wafer review sampling plan can also be generated by machine learning techniques. In this approach, historically classified defects on similar wafers are utilized as a training set to train a set of neural networks. Since this data set also has metrology values along with inspection attributes, the trained models incorporate contributions of metrology variations to defect formation. Such a trained model can then be used on other wafers to generate a review sample plan.

An inspection of the wafer with a scanning electron microscope can be performed based on the wafer review sampling plan. An inspection of a second wafer (different from a wafer that the metrology and inspection measurements are based on) also can be performed based on the wafer review sampling plan. Thus, the wafer review sampling plan can be applied to other wafers that, for example, are in the same lot, had similar manufacturing steps performed, or include similar devices.

Figure 4:
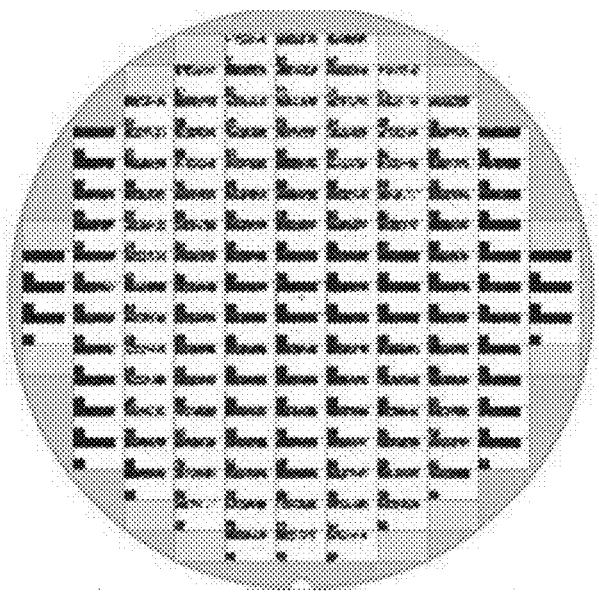
FIG. 4 is an exemplary hot optical inspection wafer map for an exemplary hotspot showing a high defect count.
Figure 5:
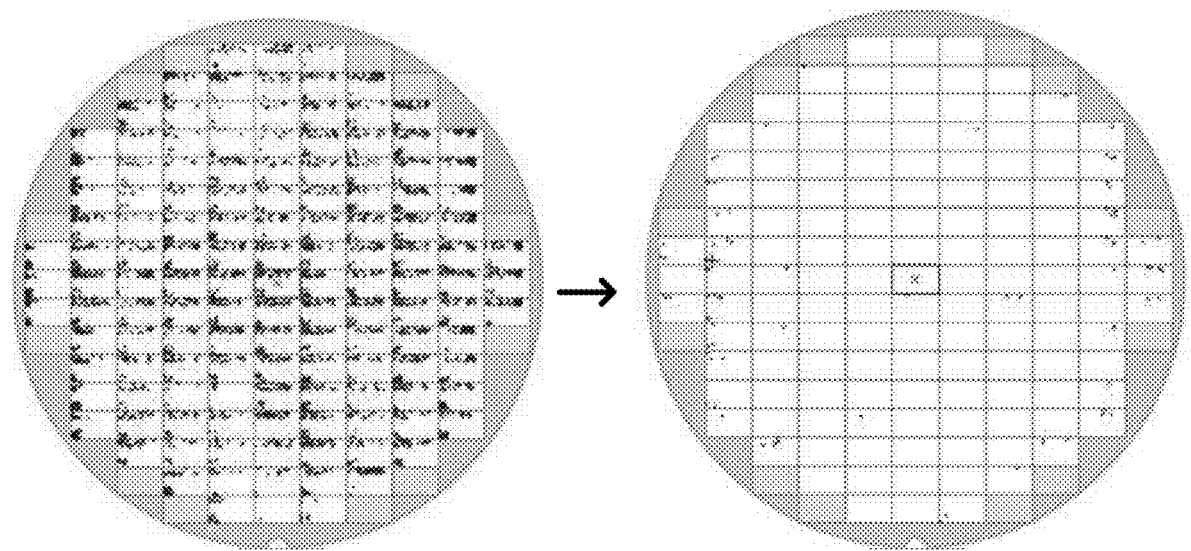
FIG. 5 shows exemplary SEM sampling of 5,000 defects using existing techniques (left) and the resulting killer defect signature with less than 100 killer defects post SEM review and classification (right)

Embodiments disclosed herein can capture unique signatures that may otherwise be missed. FIG. 4 is an exemplary optical inspection wafer map showing a high defect count. For example, this may be approximately 60,000 defects. FIG. 5 shows exemplary SEM sampling of 5,000 defects using existing techniques (left) and the killer defect signature with less than 100 killer defects (right) after SEM review and classification. A random sample would not detect all the killer defects. However, the defect distribution would be caught using an embodiment disclosed herein because the metrology data would focus (or shape) the wafer review sampling plan to the edge of the wafer rather than the center. Thus, the killer defects or other critical defects are more likely to be caught. Furthermore, a sample of, for example, only 500 defects using one of the embodiments disclosed herein can provide the same results as if 5,000 defects were sampled with the SEM. Thus, this provides a cost savings to manufacturers and increases manufacturing throughput.

The application of non-defect attributes from metrology tools to optically detected defects can improve sampling for SEM. Enhanced SEM sampling can increase chances of discovery of systematic patterning defects and can reduce false rate. During hotspot discovery, a large inspection sample is typically chosen for SEM review. This can be up to, for example, 10,000 defects. This can flag many different types of hotspots that are likely to impact yield. Thus, it may be important to limit false rate and increase weight to defects that may come from scanner, process, and/or incoming wafer quality variations. These variations are captured by various metrology such as overlay, CD, focus, dose, or topography.

Accuracy of a defined process window can be improved. If systematic defects linked to small scanner and process variations are flagged, it can provide more accurate process margins and, hence, process window.

The process window also may be expanded if systematic defects are linked to metrology data. Feedback to metrology sampling to improve effectiveness of monitoring may be provided. Additional metrology attributes can be applied to defect inspection results and in optical defect sampling.

A guided SEM review or SEM inspection without optical inspection results may be possible. A guided SEM review to flag defects without optical inspection can require navigating on a wafer without knowing where to look, which can be time consuming and impractical for reasonable wafer area coverage. Metrology data can be used to reduce this search area dramatically. Combined with design complexity and devices of interest, it is possible to localize SEM inspection or review at wafer level to search for hotspots efficiently.

In another embodiment where optical inspection has not been performed, guided SEM review inspection can be performed. In an embodiment, when nothing is known upfront about hotspots or defect types, defect discovery can still be performed solely based on metrology data. Interpolated measurements can be used to target areas of extreme variation within care areas for SEM inspection or review. In another embodiment when hotspot structures are known (e.g., from hotspot library, first pass of optical inspection, etc.), a pattern search on pre-optical proximity correction (OPC) graphic database system (GDS) (e.g., design intent on a wafer) can result in flagging all design occurrences for that hotspot. Typically, these can be thousands of occurrences per field. These locations can be sub-sampled as per metrology data for SEM review or inspection.

Figure 8:
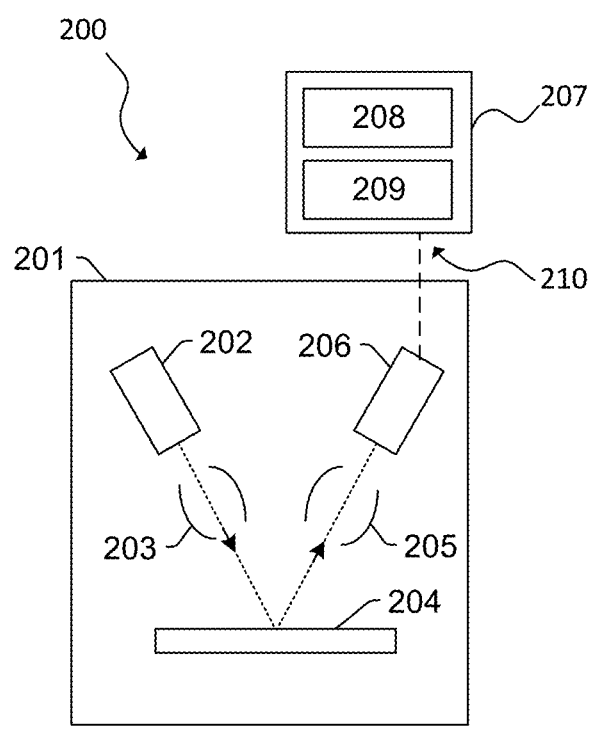
FIG. 8 is a block diagram of a system in accordance with the present disclosure.

The embodiments described herein may include or be performed in a system, such as the system 200 of FIG. 8. The system 200 includes an output acquisition subsystem that includes at least an energy source and a detector. The output acquisition subsystem may be an electron beam-based output acquisition subsystem. For example, in one embodiment, the energy directed to the wafer 204 includes electrons, and the energy detected from the wafer 204 includes electrons. In this manner, the energy source may be an electron beam source 202. In one such embodiment shown in FIG. 8, the output acquisition subsystem includes electron optical column 201, which is coupled to controller 207. The controller 207 can include one or more processors 208 and one or more memory 209. Each processor 208 may be in electronic communication with one or more of the memory 209. In an embodiment, the one or more processors 208 are communicatively coupled. In this regard, the one or more processors 208 may receive the image of the wafer 204 and store the image in the memory 209 of the controller 207. The controller 207 also may include a communication port 210 in electronic communication with at least one processor 208. The controller 207 may be part of the system 200 or may be separate from the system 200.

As also shown in FIG. 8, the electron optical column 201 includes electron beam source 202 configured to generate electrons that are focused to the wafer 204 by one or more elements 203. The electron beam source 202 may include an emitter and one or more elements 203 may include, for example, a gun lens, an anode, a beam limiting aperture, a gate valve, a beam current selection aperture, an objective lens, and/or a scanning subsystem. The electron column 201 may include any other suitable elements known in the art. While only one electron beam source 202 is illustrated, the system 200 may include multiple electron beam sources 202.

Electrons returned from the wafer 204 (e.g., secondary electrons) may be focused by one or more elements 205 to the detector 206. One or more elements 205 may include, for example, a scanning subsystem, which may be the same scanning subsystem included in element(s) 203. The electron column 201 may include any other suitable elements known in the art.

Although the electron column 201 is shown in FIG. 8 as being configured such that the electrons are directed to the wafer 204 at an oblique angle of incidence and are scattered from the wafer at another oblique angle, it is to be understood that the electron beam may be directed to and scattered from the wafer at any suitable angle. In addition, the electron beam-based output acquisition subsystem may be configured to use multiple modes to generate images of the wafer 204 (e.g., with different illumination angles, collection angles, etc.). The multiple modes of the electron beam-based output acquisition subsystem may be different in any image generation parameters of the output acquisition subsystem.

The controller 207 may be in electronic communication with the detector 206 or other components of the system 200. The detector 206 may detect electrons returned from the surface of the wafer 204 thereby forming electron beam images of the wafer 204. The electron beam images may include any suitable electron beam images. The controller 207 may be configured according to any of the embodiments described herein. The controller 207 also may be configured to perform other functions or additional steps using the output of the detector 206 and/or the electron beam images. For example, the controller 207 may be programmed to perform some or all of the steps of FIG. 1. For example, the controller 207 may receive metrology measurements and inspection measurements of a wafer and can be programmed to interpolate and/or extrapolate the metrology measurements over a field of the wafer thereby creating modified metrology data; associate defect attributes from the inspection measurements with the modified metrology data; and generate a wafer review sampling plan based on the defect attributes and the modified metrology data. The controller 207 also can send instructions to execute a wafer review sampling plan. For example, the controller 207 can transmit the wafer review sampling plan to the system 200, which may be a scanning electron microscope.

It is to be appreciated that the controller 207 may be implemented in practice by any combination of hardware, software, and firmware. Also, its functions as described herein may be performed by one unit, or divided up among different components, each of which may be implemented in turn by any combination of hardware, software, and firmware. Program code or instructions for the controller 207 to implement various methods and functions may be stored in controller readable storage media, such as a memory 209, within the controller 207, external to the controller 207, or combinations thereof.

It is noted that FIG. 8 is provided herein to generally illustrate a configuration of an electron beam-based output acquisition subsystem. The electron beam-based output acquisition subsystem configuration described herein may be altered to optimize the performance of the output acquisition subsystem as is normally performed when designing a commercial output acquisition system. In addition, the system described herein or components thereof may be implemented using an existing system (e.g., by adding functionality described herein to an existing system). For some such systems, the methods described herein may be provided as optional functionality of the system (e.g., in addition to other functionality of the system).

While disclosed as part of a defect review system, the controller 207 or methods described herein may be configured for use with inspection systems. In another embodiment, the controller 207 or methods described herein may be configured for use with a metrology system. Thus, the embodiments as disclosed herein describe some configurations for classification that can be tailored in a number of manners for systems having different imaging capabilities that are more or less suitable for different applications.

In particular, the embodiments described herein may be installed on a computer node or computer cluster that is a component of or coupled to the detector 206 or another component of a defect review tool, a mask inspector, a virtual inspector, or other devices. In this manner, the embodiments described herein may generate output that can be used for a variety of applications that include, but are not limited to, wafer inspection, mask inspection, electron beam inspection and review, metrology, or other applications. The characteristics of the system 200 shown in FIG. 8 can be modified as described above based on the specimen for which it will generate output.

The controller 207, other system(s), or other subsystem(s) described herein may take various forms, including a personal computer system, workstation, image computer, mainframe computer system, workstation, network appliance, internet appliance, parallel processor, or other device. In general, the term "controller" may be broadly defined to encompass any device having one or more processors that executes instructions from a memory medium. The subsystem(s) or system(s) may also include any suitable processor known in the art, such as a parallel processor. In addition, the subsystem(s) or system(s) may include a platform with high speed processing and software, either as a standalone or a networked tool.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

In another embodiment, the controller 207 may be communicatively coupled to any of the various components or sub-systems of system 200 in any manner known in the art. Moreover, the controller 207 may be configured to receive and/or acquire data or information from other systems (e.g., inspection results from an inspection system such as a BBP tool, a remote database including design data and the like) by a transmission medium that may include wired and/or wireless portions. In this manner, the transmission medium may serve as a data link between the controller 207 and other subsystems of the system 200 or systems external to system 200.

The controller 207 may be coupled to the components of the system 200 in any suitable manner (e.g., via one or more transmission media, which may include wired and/or wireless transmission media) such that the controller 207 can receive the output generated by the system 200. The controller 207 may be configured to perform a number of functions using the output. In another example, the controller 207 may be configured to send the output to a memory 209 or another storage medium without performing defect review on the output. The controller 207 may be further configured as described herein.

An additional embodiment relates to a non-transitory computer-readable medium storing program instructions executable on a controller for performing a computer-implemented method for aligning an SEM system, as disclosed herein. In particular, as shown in FIG. 8, the controller 207 can include a memory 209 or other electronic data storage medium with non-transitory computer-readable medium that includes program instructions executable on the controller 207. The computer-implemented method may include any step(s) of any method(s) described herein. The memory 209 or other electronic data storage medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), SSE (Streaming SIMD Extension), or other technologies or methodologies, as desired.

In some embodiments, various steps, functions, and/or operations of system 200 and the methods disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape and the like. A carrier medium may include a transmission medium such as a wire, cable, or wireless transmission link. For instance, the various steps described throughout the present disclosure may be carried out by a single controller 207 (or computer system) or, alternatively, multiple controllers 207 (or multiple computer systems). Moreover, different sub-systems of the system 200 may include one or more computing or logic systems. Therefore, the above description should not be interpreted as a limitation on the present invention but merely an illustration.

As used throughout the present disclosure, a "wafer" may refer to a substrate formed of a semiconductor or non-semiconductor material. For example, a semiconductor or non-semiconductor material may include, but is not limited to, monocrystalline silicon, gallium arsenide, or indium phosphide. A wafer may include one or more layers. For example, such layers may include, but are not limited to, a resist, a dielectric material, a conductive material, or a semiconductive material. Many different types of such layers are known in the art, such as, but not limited to, isolation layers, implantation layers, and the like. The term "wafer" as used herein is intended to encompass a substrate on which any of such layers may be formed.

Each of the steps of the method may be performed as described herein. The methods also may include any other step(s) that can be performed by the controller and/or computer subsystem(s) or system(s) described herein. The steps can be performed by one or more computer systems, which may be configured according to any of the embodiments described herein. In addition, the methods described above may be performed by any of the system embodiments described herein.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A method comprising:
   receiving metrology measurements and inspection measurements at a controller, wherein the metrology measurements and inspection measurements are of one or more wafers;
   interpolating and/or extrapolating, using the controller, the metrology measurements over a field of a wafer thereby creating modified metrology data, wherein the field encompasses devices across a surface of the wafer, and wherein the modified metrology data is a uniform grid across the surface of the wafer;
   associating, using the controller, defect attributes from the inspection measurements with the modified metrology data, wherein the modified metrology data includes an overlay vector; and
   generating, using the controller, a wafer review sampling plan that is weighted based on highest variation in the defect attributes and the modified metrology data.

2. The method of claim 1, further comprising performing an inspection of the wafer with a scanning electron microscope based on the wafer review sampling plan.

3. The method of claim 1, further comprising performing an inspection of a different wafer with a scanning electron microscope based on the wafer review sampling plan for the wafer.

4. The method of claim 1, wherein the interpolating occurs, and wherein the interpolating includes local linear interpolation.

5. The method of claim 1, wherein the interpolating occurs, and wherein the metrology measurements are for an entire surface of the wafer and the interpolating is across the entire surface of the wafer.

6. The method of claim 1, wherein the metrology measurements include at least one of overlay, dose, focus, critical dimension, and topography.

7. The method of claim 1, wherein the interpolating occurs, and wherein the interpolating includes a model based approach.

8. The method of claim 1, wherein the field is an entire surface of the wafer.

9. A system comprising:
   a controller in electronic communication with a scanning electron microscope and a metrology tool, wherein the controller includes a processor and an electronic data storage unit in electronic communication with the processor, and wherein the controller is configured to:
   receive metrology measurements and inspection measurements of one or more wafers;
   interpolate and/or extrapolate the metrology measurements over a field of a wafer thereby creating modified metrology data, wherein the field encompasses devices across a surface of the wafer, and wherein the modified metrology data is a uniform grid across the surface of the wafer;
   associate defect attributes from the inspection measurements with the modified metrology data, wherein the modified metrology data includes an overlay vector; and
   generate a wafer review sampling plan that is weighted based on highest variation in the defect attributes and the modified metrology data.

10. The system of claim 9, wherein the controller is further configured to transmit the wafer review sampling plan to the scanning electron microscope.

11. The system of claim 9, wherein the metrology measurements include at least one of overlay, dose, focus, critical dimension, and topography.

12. A non-transitory computer readable medium storing a program configured to instruct a processor to:
   interpolate and/or extrapolate metrology measurements of one or more wafers over a field of a wafer thereby creating modified metrology data, wherein the field encompasses devices across a surface of the wafer, and wherein the modified metrology data is a uniform grid across the surface of the wafer;
   associate defect attributes from inspection measurements of the wafer with the modified metrology data, wherein the modified metrology data includes an overlay vector; and
   generate a wafer review sampling plan that is weighted based on highest variation in the defect attributes and the modified metrology data.

13. The non-transitory computer readable medium of claim 12, wherein the interpolating occurs, and wherein the interpolating includes local linear interpolation.

14. The non-transitory computer readable medium of claim 12, wherein the interpolating occurs, and wherein the metrology measurements are for an entire surface of the wafer and the interpolating is across the entire surface of the wafer.

15. The non-transitory computer readable medium of claim 12, wherein the metrology measurements include at least one of overlay, dose, focus, critical dimension, and topography.

16. The non-transitory computer readable medium of claim 12, wherein the interpolating occurs, and wherein the interpolating includes a model based approach.

* * * * *